(12) United States Patent
Boyd et al.

(10) Patent No.: US 8,334,380 B2
(45) Date of Patent: Dec. 18, 2012

(54) METHOD FOR PRODUCING BICYCLIC GUANIDINES BY USE OF A CYCLIC UREA AND A DEHYDRATING AGENT

(75) Inventors: Donald W. Boyd, Cheswick, PA (US); Venkatachalam Eswarakrishnan, Allison Park, PA (US); Charles R. Hickenboth, Cranberry Township, PA (US); Richard F. Karabin, Ruffs Dale, PA (US); Gregory J. McCollum, Gibsonia, PA (US); Britt A. Minch, Tarentum, PA (US); Thomas C. Moriarity, Allison Park, PA (US); Steven R. Zawacky, Pittsburgh, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 960 days.

(21) Appl. No.: 12/195,751

(22) Filed: Aug. 21, 2008

(65) Prior Publication Data

US 2009/0281314 A1    Nov. 12, 2009

Related U.S. Application Data

(63) Continuation-in-part of application No. 12/118,082, filed on May 9, 2008, now Pat. No. 8,039,618.

(51) Int. Cl.
*C07D 471/04* (2006.01)
(52) U.S. Cl. ......................................................... 544/279
(58) Field of Classification Search .................. 544/279
See application file for complete search history.

(56) References Cited

U.S. PATENT DOCUMENTS

2006/0276461 A1 * 12/2006 Old et al. .................. 514/227.2

FOREIGN PATENT DOCUMENTS

WO    2011/079041    6/2011

OTHER PUBLICATIONS

Margetic, et al., Synthetic Communications, vol. 41, # 15, 2011.*

* cited by examiner

*Primary Examiner* — Cecilia M Jaisle
(74) *Attorney, Agent, or Firm* — Diane R. Meyers; Alicia Pascerin

(57) ABSTRACT

The present invention is directed to a method for producing bicyclic guanidines comprising heating a reaction mixture comprising cyclic urea and a dehydrating agent to a temperature ≧90° C.

18 Claims, No Drawings

METHOD FOR PRODUCING BICYCLIC GUANIDINES BY USE OF A CYCLIC UREA AND A DEHYDRATING AGENT

CROSS REFERENCE TO RELATED APPLICATIONS

This application is a continuation-in-part application of U.S. patent application Ser. No. 12/118,082, which was filed on May 9, 2008.

BACKGROUND OF THE INVENTION

1. Field of the Invention

The present invention relates to a method for producing bicyclic guanidines.

2. Background Information

Bicyclic guanidines, such as 1,5,7-triazabicyclo[4.4.0]dec-5-ene (TBD), are chemically active and, therefore, can be used to catalyze a variety of chemical reactions. An important consideration in the commercial exploitation of bicyclic guanidines as a catalyst (for any reaction) is that bicyclic guanidines be relatively inexpensive to purchase or easily produced. Published methods for synthesizing bicyclic guanidines, however, are often complicated, often involve the use of a multiple step synthesis process, and/or require the use of prohibitively expensive starting materials which may be hazardous in a variety of ways.

For example, some methods utilize carbon disulfide ($CS_2$) in the production of bicyclic guanidines. However, there are regulatory and handling issues associated with the use of carbon disulfide. For instance, air transport of carbon disulfide is typically prohibited. Additionally, contact with carbon disulfide with air should be avoided because the combination of high volatility, wide flammability range, and low ignition temperature results in a readily combustible mixture.

Accordingly, there is a need for a process for producing bicyclic guanidines at relatively high yields while not using hazardous materials, such as carbon disulfide, as an ingredient to produce the bicyclic guanidines.

SUMMARY OF THE INVENTION

The present invention is directed to a method for producing bicyclic guanidines comprising heating a reaction mixture comprising cyclic urea and a dehydrating agent to a temperature $\geq 90°$ C. The present invention is further directed to an electrodepositable coating composition comprising bicyclic guanidine made by the aforementioned method.

The present invention is also directed to a method for producing bicyclic guanidines comprising heating a reaction mixture comprising cyclic urea and a dehydrating agent to a temperature $\geq 90°$ C. in the presence of a non-hydrocarbon solvent.

DETAILED DESCRIPTION OF THE INVENTION

As used herein, unless otherwise expressly specified, all numbers such as those expressing values, ranges, amounts or percentages may be read as if prefaced by the word "about", even if the term does not expressly appear. Plural encompasses singular and vice versa. For example, although reference is made herein to "an" (aminoalkyl) amine, "a" carbonate, a combination (i.e., a plurality) of (aminoalkyl) amines and/or carbonates may be used.

As used herein, "plurality" means two or more.

As used herein, "includes" and like terms means "including without limitation."

When referring to any numerical range of values, such ranges are understood to include each and every number and/or fraction between the stated range minimum and maximum.

The present invention is directed towards a method of producing bicyclic guanidines. Specifically, the present invention is directed towards a method of producing bicyclic guanidines that comprises heating a reaction mixture comprising cyclic urea and a dehydrating agent to a temperature $\geq 90°$ C. In some embodiments, the reaction mixture is heated to a temperature that is $\leq 230°$ C. In certain embodiments, the temperature to which the reaction mixture is heated can range between any combination of values, which were recited in the preceding sentences, inclusive of the recited values. For example, in certain embodiments, the temperature can range from 90° C. to 230° C., such as from 100° C. to 200° C.

In certain embodiments, the molar ratio of dehydrating agent to cyclic urea can be $\geq 0:1$. In some embodiments, the molar ratio of dehydrating agent to cyclic urea to dehydrating agent can be $\leq 2:1$. In other embodiments, the molar ratio of dehydrating agent to cyclic urea can range between any combination of values, which were recited in the preceding sentences, inclusive of the recited values. For example, in certain embodiments, the molar ratio can range from 0.25 to 2:1 or from 1:8 to 1:2.

Suitable dehydrating agents that may be used in the present invention include, without limitation, hexamethyldisilazane (HDMS), tetraethoxysilane (TEOS), disilazane (e.g., alkyl disilazine), alkoxy substituted silane (e.g., tetraethoxysilane), or combinations thereof.

In certain embodiments, the cyclic urea that is used in the present invention is formed by reacting an (aminoalkyl) amine with a carbonate.

As used herein, the term "(aminoalkyl) amine" refers generally to a compound having the formula $H_2N(CR^3R^4)_n NH(CR^5R^6)_m NH_2$ wherein n and m are independently integers having a value in the range from 2 to 6 and wherein $R^3$, $R^4$, $R^5$, and $R^6$ are independently hydrogen or substituted or unsubstitued alkyl or aryl groups. In addition, the composition of each individual —$CR^3R^4$— and —$CR^5R^6$— unit may also differ from one another. For example, in certain embodiments the $R^3$ group may comprise —$CH_2$— while the R5 group may comprise —$CH_2CH_2CH_2$—. Particularly, suitable (aminoalkyl) amines are those where $R^3$, $R^4$, $R^5$, and $R^6$ are independently hydrogen or a $C_1$-$C_3$ alkyl group. Suitable (aminoalkyl) amines within the formula described in this paragraph and which may be used in the present invention include, without limitation, bis(2-aminoethyl)amine, bis(3-aminopropyl)amine, or combinations thereof.

Suitable carbonates that may be used in the present invention include, without limitation, dialkyl and alkylene carbonates such as propylene carbonate, dimethyl carbonate, diethyl carbonate, ethylene carbonate, or combinations thereof.

In certain embodiments, the reaction occurs in a non-hydrocarbon solvent, such as an ethereal solvent. Suitable ethereal solvents that may be utilized in the present invention include, without limitation, triethlyene glycol dimethyl ether, diethylene glycol dibutyl ether, tetraethylene glycol dimethyl ether, butyl carbitol formal, or combinations thereof. Suitable glycol ethers that may be used in the present invention include, without limitation, diethylene glycol monobutyl ether, dipropylene glycol monobutyl ether, propylene glycol butyl ether, or combinations thereof. It should be understood that lower molecular weight, lower boiling ethers that are known in the art can be used in the present invention by running the reaction under pressure, such as up to 2500 psig.

It should be noted that, in certain embodiments, the reaction mixture that is used to form the cyclic urea can include a hydrocarbon solvent, such as xylene, in addition to the non-hydrocarbon solvent described above. Alternatively, in certain embodiments, the reaction mixture that is used to form the cyclic urea is substantially solvent free. As used herein, "substantially solvent free" means that trace or incidental amounts of organic solvent, such as $\leq 5$ weight % or $\leq 3$ weight % or $\leq 1$ weight % based on all of the ingredients used in the reaction mixture, can be present.

In certain embodiments, a catalyst, such as an acid or base catalyst, can be added to the reaction mixture of the (aminoalkyl) amine and the carbonate. Any catalyst known in the art may be used. For example, suitable catalysts include, without limitation, mineral acids (e.g., hydrogen chloride, hydrogen bromide, sulfuric acid and phosphoric acid), organic acids (e.g., p-toluenesulfonic acid (PTSA)), Lewis acids (e.g., boron trifluoride etherate, aluminum trichloride, and alkaline and/or alkaline earth metals), dimethylaminopyridine, imidazole, 1,5,7-triazabicyclo[4.4.0]dec-5-ene, or combinations thereof.

In certain embodiments, the process begins by charging a reaction vessel with the (aminoalkyl) amine and a solvent. The solvent can either be a hydrocarbon solvent, such as xylene, or a non-hydrocarbon solvent, such as dipropylene glycol monobutyl ether. In certain embodiments, no solvent is added with the (aminoalkyl) amine. In some embodiments, the dehydrating agent may be added to the reaction vessel at this time. However, as will be described in further detail below, the dehydrating agent may also be added later in the process, such as after the formation of the cyclic urea. Accordingly, in some embodiments, the dehydrating agent is added to the reaction vessel: (i) when the reaction vessel is charged with the (aminoalkyl) amine and solvent; (ii) after the formation of the cyclic urea; or (iii) when the reaction vessel is charged with the (aminoalkyl) amine and solvent as well as after the formation of the cyclic urea.

The total amount of carbonate that may be added to the reaction vessel will depend upon the total amount of (aminoalkyl) amine used in the reaction and can, therefore, be any value, and the rate at which the carbonate is added will be dependent upon the total amount of carbonate that will be added to the reaction vessel. For example, in certain embodiments, the carbonate is added dropwise to this reaction vessel at a rate ranging from 3 grams (g)/minute to 5 g/minute for a total weight ranging from 120 g to 130 g, such as 124 g.

The reaction vessel is then heated to a temperature and a time period that is sufficient to form the cyclic urea reaction product. In certain embodiments, the reaction vessel is heated to a temperature ranging from $\geq 80°$ C., such as from 80° C. to 100° C., for a time period ranging from 1 hour to 2 hours. After this initial heating step, a non-hydrocarbon solvent, such as those described above, is added to the reaction vessel. The reaction vessel is then heated to $\geq 130°$ C. for a time period ranging from 1 hour to 2 hours thereby forming the cyclic urea reaction product.

If a hydrocarbon solvent was used in the steps to form the cyclic urea, it should be noted that the hydrocarbon solvent would be distilled from the reaction vessel prior to the step wherein the bicyclic guanidine reaction product is formed. Accordingly, one skilled in the art would recognize that the formation of the bicyclic reaction product occurs in the substantially non-hydrocarbon solvent.

The bicyclic guanidine reaction product is formed by heating the reaction vessel, which contains the cyclic urea formed in the preceding paragraphs, to a temperature $\geq 90°$ C., such as from 100° C. or 230° C., then heating the reactive mixture to reflux for a time period ranging from 10 hours to 50 hours, such as 20 hours to 40 hours. As stated above, in certain embodiments, the dehydrating agent is added to the reaction vessel during this step.

After the bicyclic guanidine is formed, it can be isolated by removing the non-hydrocarbon solvent from the reaction vessel. It should also be noted that additional filtration steps, such as a filtration step used to remove any silica that is produced during the process when alkoxy silanes are used, may be required in order to isolate the bicyclic guanidine. The isolated bicyclic guanidine, which would be in solid form, can then be added to any composition wherein bicyclic guanidine can be used therein. It should also be noted that bicyclic guanidine can also be isolated via precipitation and/or crystallization. Accordingly, in certain embodiments, a solvent, such as heptanes, hexanes, or combinations thereof, is added in which the bicyclic guanidine is insoluble thereby precipitating the bicyclic guanidine.

Alternatively, unisolated bicyclic guanidine may also be admixed with any composition, such as a coating composition, wherein bicyclic guanidine can be used therein. Accordingly, in certain embodiments, the unisolated bicyclic guanidine is cooled to room temperature and a diluent, such as a high-boiling point diluent, is added to the reaction vessel prior to removing the non-hydrocarbon solvent from the reaction vessel. Suitable diluents that may be used in this step include, without limitation, ethoxylated bisphonol A, butyl carbitol formal, or combinations thereof. After removing the non-hydrocarbon solvent from the reaction vessel, the mixture of bicyclic guanidine and diluent may then be admixed with a coating composition, such as an electrodepositable coating composition that is known in the art. For example, in certain embodiments, the bicyclic guanidine formed from the process described herein can be used in the electrodepositable coating composition that is described in U.S. patent application Ser. No. 11/835,600, which is incorporated in its entirety herein by reference.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the claims appended and any and all equivalents thereof.

EXAMPLES

Example 1

A 1000 mL flask equipped with a reflux condenser, was purged with nitrogen, and was charged with 3,3'-diaminodipropylamine (100.0 g, 763 mmol), dimethyl carbonate (70.0 g, 770 mmol) and a catalytic amount of 1,5,7-triazabicyclo[4.4.0]dec-5-ene (7.0 g, 50 mmol). The mixture was refluxed at 90° C. for 2 hours (h), the rxn vessel was then fit with a distillation apparatus, and the mixture was warmed to 130° C. and methanol was distilled off. The reaction was cooled when no more distillate was observed and the reaction mixture was diluted with 400 mL of butyl carbitol formal. The reaction was reheated to 230° C. and Tetraethyl ortho silicate was slowly added via an addition funnel. The reaction was held at 230° C. for 16 h. The conversion to 1,5,7-triazabicyclo

[4.4.0]dec-5-ene from the urea intermediate was followed by quantitative $^{13}$C NMR; the conversion was 86%.

Example 2

A 100 mL flask equipped with a reflux condenser and distillation apparatus was purged with nitrogen and was charged with 3,3'-diaminodipropylamine (10 g, 80 mmol), dimethyl carbonate (6.9 g, 80 mmol) and a catalytic amount of 1,5,7-triazabicyclo[4.4.0]dec-5-ene (0.53 g, 3.8 mmol). The mixture was warmed to 130° C. and methanol was distilled out. The reaction was cooled when no more distillate was observed. The resulting light orange oil was identified as N-(3-aminopropyl)-N,N'-trimethyleneurea by $^{13}$C NMR.

Example 3

A 100 mL flask equipped with a reflux condenser was purged with nitrogen and was charged with N-(3-aminopropyl)-N,N'-trimethyleneurea (2.6 g, 17 mmol), HMDS (3.21 g, 20 mmol), toluene sulfonic acid (0.32 g, 2 mmol) and dichlorobenzene (21 g). The resulting mixture was warmed to reflux and held for 50 h. The conversion to 1,5,7-triazabicyclo [4.4.0]dec-5-ene from the starting urea by quantitative $^{13}$C NMR was 78%.

What is claimed is:

1. A method for producing 1,5,7-triazabicyclo[4.4.0]dec-5-ene comprising heating a reaction mixture comprising cyclic urea and a dehydrating agent to a temperature $\geq$90° C., wherein the cyclic urea is a reaction product of bis(3-aminopropyl) amine and a carbonate, wherein the carbonate comprises propylene carbonate, dimethyl carbonate, diethyl carbonate, ethylene carbonate, or combinations thereof.

2. The method according to claim 1, wherein the temperature is $\leq$230° C.

3. The method according to claim 1, wherein the dehydrating agent comprises hexamethyldisilazane, tetraethoxysilane, disilazane, tetraalkoxy silane, or combinations thereof.

4. The method according to claim 1, wherein the dehydrating agent is added to the mixture comprising the bis(3-aminopropyl) amine and the carbonate.

5. The method according to claim 1, wherein the method further comprises adding a catalyst to the mixture comprising the bis(3-aminopropyl) amine and the carbonate.

6. The method according to claim 5, wherein the catalyst is an acid catalyst.

7. The method according to claim 6, wherein the acid catalyst comprises mineral acids, organic acids, Lewis acids, or combinations thereof.

8. The method according to claim 5, wherein the catalyst is a base catalyst.

9. The method according to claim 8, wherein the base catalyst comprises dimethylaminopyridine, imidazole, 1,5,7-triazabicyclo[4.4.0]dec-5-ene, or combinations thereof.

10. The method according to claim 1, wherein the reaction of the bis(3-aminopropyl) amine and the carbonate occurs in an ethereal solvent.

11. The method according to claim 10, wherein the ethereal solvent comprises triethlyene glycol dimethyl ether, diethylene glycol dibutyl ether, diethylene glycol monobutyl ether, tetraethylene glycol dimethyl ether, diphenyl ether, or combinations thereof.

12. The method according to claim 1, wherein the molar ratio of dehydrating agent to cyclic urea ranges from >0 to 2:1.

13. A method for producing 1,5,7-triazabicyclo[4.4.0]dec-5-ene comprising:
reacting bis(3-aminopropyl) amine and a carbonate to form a cyclic urea, wherein the carbonate comprises propylene carbonate, dimethyl carbonate, diethyl carbonate, ethylene carbonate, and/or combinations thereof in the presence of an ethereal solvent or an alcohol; and
heating a reaction mixture comprising the cyclic urea and a dehydrating agent to a temperature $\geq$90° C.

14. The method according to claim 13, wherein the method further comprises adding a catalyst to the reaction mixture of the bis(3-aminopropyl) amine and the carbonate.

15. The method according to claim 13, wherein the dehydrating agent is added to the mixture of the bis(3-aminopropyl) amine and the carbonate.

16. The method according to claim 13, wherein the cyclic urea is formed by heating the bis(3-aminopropyl) amine and the carbonate to a temperature $\geq$80° C.

17. The method according to claim 13, wherein the dehydrating agent comprises hexamethyldisilazane, tetraethoxysilane, disilazane, tetraalkoxy silane or combinations thereof.

18. The method according to claim 13, further comprising adding a diluent to the 1,5,7-triazabicyclo[4.4.0]dec-5-ene, wherein the diluent comprises ethoxylated bisphenol A, butyl carbitol formal, or combinations thereof; and removing the ethereal solvent and/or the alcohol.

* * * * *